United States Patent
Kasinathan et al.

(10) Patent No.: US 10,927,411 B2
(45) Date of Patent: Feb. 23, 2021

(54) METHODS FOR GENERATING ANIMALS WITH DESIRABLE TRAITS

(71) Applicant: Trans Ova Genetics, L.C., Sioux Center, IA (US)

(72) Inventors: Poothappillai K. Kasinathan, Brandon, SD (US); Hong Wei, Sioux Falls, SD (US); Mark F. Allan, Le Mars, IA (US); David C. Faber, Sioux City, IA (US)

(73) Assignee: TRANS OVA GENETICS, L.C., Sioux Center, IA (US)

( * ) Notice: Subject to any disclaimer, the term of this patent is extended or adjusted under 35 U.S.C. 154(b) by 0 days.

(21) Appl. No.: 14/436,664

(22) PCT Filed: Oct. 18, 2013

(86) PCT No.: PCT/US2013/065618
§ 371 (c)(1),
(2) Date: Apr. 17, 2015

(87) PCT Pub. No.: WO2014/063016
PCT Pub. Date: Apr. 24, 2014

(65) Prior Publication Data
US 2015/0247197 A1    Sep. 3, 2015

Related U.S. Application Data (60) Provisional application No. 61/716,294, filed on Oct. 19, 2012.

(51) Int. Cl.
| | |
|---|---|
| *C12Q 1/68* | (2018.01) |
| *C12N 15/85* | (2006.01) |
| *A01K 67/00* | (2006.01) |
| *C12Q 1/6883* | (2018.01) |
| *A01K 67/027* | (2006.01) |
| *A01K 67/02* | (2006.01) |

(52) U.S. Cl.
CPC ............ *C12Q 1/6883* (2013.01); *A01K 67/02* (2013.01); *A01K 67/0273* (2013.01); *A01K 2207/00* (2013.01); *A01K 2227/101* (2013.01); *A01K 2267/02* (2013.01); *C12Q 2600/124* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 6,011,197 A | * | 1/2000 | Strelchenko | C12N 5/0603 435/325 |
| 2006/0008807 A1 | * | 1/2006 | O'Hara | C12N 1/06 435/6.14 |
| 2008/0085836 A1 | * | 4/2008 | Kearns | C40B 20/00 506/2 |
| 2009/0075380 A1 | | 3/2009 | Smith et al. | |

FOREIGN PATENT DOCUMENTS

| | | |
|---|---|---|
| CA | 2368620 | 11/2000 |
| CN | 1715401 | 1/2006 |
| CN | 101024829 | 8/2007 |
| WO | WO-01/50848 A2 | 7/2001 |

OTHER PUBLICATIONS

Choi et al, Viability of quine embryosafter puncture of the capsule and biopsy for preimplantation genetic diagnosis, Reproduction, 2010, pp. 893-902.*
Kitiyanant et al, Sex Determination by Polymerase Chain Reaction and Karyotyping of Bovine Embryos at First Cleavage in vitro, ScienceAsia, 2002, apges 9-13.*
Natale et al, Sensitivity of bovine blastocyst gene expression patterns to culture environments assessed by differential display RT-PCR, Obstetrics and Gynaecology Publications, 2001, pp. 1-32.*
Winger et al, Genetic Reprogramming of Lactate Dehydrogenase, Citrate Synthase, and Phosphofructokinase mRNA in Bovine Nuclear Transfer Embryos Produced Using Bovine, Molecular Reproduction and Development 56:458±464 (2000).*
Alexopoulous and French the prevalence of embryonic remnants following the recovery of post-hatching bovine embryos produced in vitro or by somatic cell nuclear transfer, Animal Reproduction Science 114 (2009) 43-53.*
Ji et al, Preclinical Study of Preimplnatation Genetic Diagnosis in Animal, Zhonghua Fu Chan Ke Za Zhi, 2000, pp. 462-464 (Chinese version, English abstract).*
Ji et al, Preclinical Study of Preimplnatation Genetic Diagnosis in Animal, Zhonghua Fu Chan Ke Za Zhi, 2000, 1 page English summary.*
Guyader-Joly et al, 135 Pregnancy Rates After Single Direct Transfer of Biopsied Frozen-Thawed Bovine Embryos According to Quality, Reproduction, 2008, p. 167.*
Basille et al., "Preimplantation genetic diagnosis: state of the art," Eur J Obstet Gynecol Reprod Biol. 145(1):9-13 (2009).
Bourhis et al., "135 Breeding Values Concordance Between Embryos and Corresponding Calves," Reprod Fertil Dev. 24(1):180 (2011).
Bourhis et al., "187 Embryo Genotyping From in Vivo Biopsied Bovine Embryos After Whole Genome Amplification," Reprod Fertil Dev. 21(1):192 (2008).

(Continued)

*Primary Examiner* — Maria Marvich
(74) *Attorney, Agent, or Firm* — Gene J. Yao; Barnes & Thornburg LLP (57) ABSTRACT

Genetic tests, such as whole genome analysis (WGA), have been employed to identify genetically superior embryos. The disclosed methods extend in vitro culture time of embryos while awaiting results of genetic tests being performed on a portion of the same embryos. The disclosed methods also help expand the number of cells in each embryo before implantation in the recipient.

14 Claims, 2 Drawing Sheets

(56) References Cited

OTHER PUBLICATIONS

Bourhis et al., "193 Bovine Embryo Genotyping Using a 50K Single Nucleotide Polymorphism Chip," Reprod Fertil Dev. 23(1):197 (2010).
Cenariu et al., "Evaluation of bovine embryo biopsy techniques according to their ability to preserve embryo viability," J Biomed Biotechnol. 2012:541384 (2012) (5 pages).
Choi et al., "Viability of equine embryos after puncture of the capsule and biopsy for preimplantation genetic diagnosis," Reproduction. 140(6):893-902 (2010).
Fisher et al., "Brief communication: potential for genomic selection of bovine embryos," Proceedings of the New Zealand Society of Animal Production. 72:156-8 (2012).
Humblot et al., "Reproductive technologies and genomic selection in cattle," Vet Med Int. 2010:192787 (2010) (8 pages).
Humblot, "Reproductive technologies and epigenetics: their implications for genomic selection in cattle," Acta Scientiae Veterinariae. 39(Suppl 1):s253-62 (2011).
Kasinathan et al., "Acceleration of genetic gain in cattle by reduction of generation interval," Sci Rep. 5:8674 (2015).
Ponsart et al., "Embryo genotyping: from DNA Amplification to field implementation," 28th Annual Meeting A.E.T.E. Sep. 7-8, Saint Malo, France. 83-93 (2012).
Arny et al., "The effect of preimplantation culture conditions on murine embryo implantation and fetal development," Fertil Steril. 48(5):861-5 (1987) (Abstract only).
Braude et al., "Preimplantation genetic diagnosis," Nat Rev Genet. 3(12):941-53 (2002).
International Search Report and Written Opinion for International Patent Application No. PCT/US2013/065618, dated Jan. 17, 2014 (11 pages).
International Preliminary Report on Patentability for International Patent Application No. PCT/US2013/065618, dated Apr. 21, 2015 (6 pages).
Galli et al., "Bovine embryo technologies," Theriogenology. 59(2):599-616 (2003).
Lauri et al., "Assessment of MDA efficiency for genotyping using cloned embryo biopsies," Genomics. 101(1):24-9 (2013).

\* cited by examiner

METHODS FOR GENERATING ANIMALS WITH DESIRABLE TRAITS

BACKGROUND OF THE INVENTION

The present disclosure pertains to methods for animal production. More particularly, the disclosure pertains to selective production of animals that have certain desirable traits.

Traditional methods of selecting genetically superior animals typically involve breeding two animals and testing the resulting progeny to identify the best sires for widespread use. While this method is reliable, it has major disadvantages. For instance, it typically takes several years from conception to completion of the progeny test. Traditional methods are also associated with high degree of waste and high cost because only 10% of the bulls are selected as the final product. The advent of genomic selection techniques allows breeders to identify genetically superior animals at an age that is earlier than that of traditional methods. For instance, various molecular tests may be performed at different stages prior to birth to identify offspring with desirable traits.

There are several practical ways to improve the process of selecting superior male and female cattle having important traits. These methods include, for example, (1) increasing the accuracy of selection; (2) increasing the selection intensity; and/or (3) decreasing the generation interval. Generation interval typically refers to the average age of parents when the offspring are born. Generation interval is the most important factor that affects the rate of genetic progress in breeding programs. The shortest possible generation interval is the sum of age at sexual maturity and generation length. A number of techniques may be used to circumvent the limitation imposed by generation interval. For example, advanced reproductive technologies such as ovum pick-up from pre-pubertal young heifers, in vitro fertilization (IVF), and whole genome evaluation of the resultant embryos have been used to shorten generation interval.

Although oocyte collection from pre-pubertal heifers may be used to shorten generation interval, the quality of the oocytes collected in such a manner is generally poor and tend to produce low quality embryos. Most whole genome analyses require collection of some embryonic cells of an embryo by embryonic biopsy, which may be intrusive and may compromise the developmental potential of the embryos. Moreover, whole genome analysis of the biopsied sample may take weeks, which necessitates freezing of embryos or transfer of embryos to recipients before the results of the whole genome analysis are known.

SUMMARY OF THE INVENTION

The present invention provides improved methods for selecting embryos having desirable traits. In one embodiment, methods for expanding the cell numbers of embryos for genomic evaluation and production of offspring are disclosed.

Figures 1A, 1B, 1C:
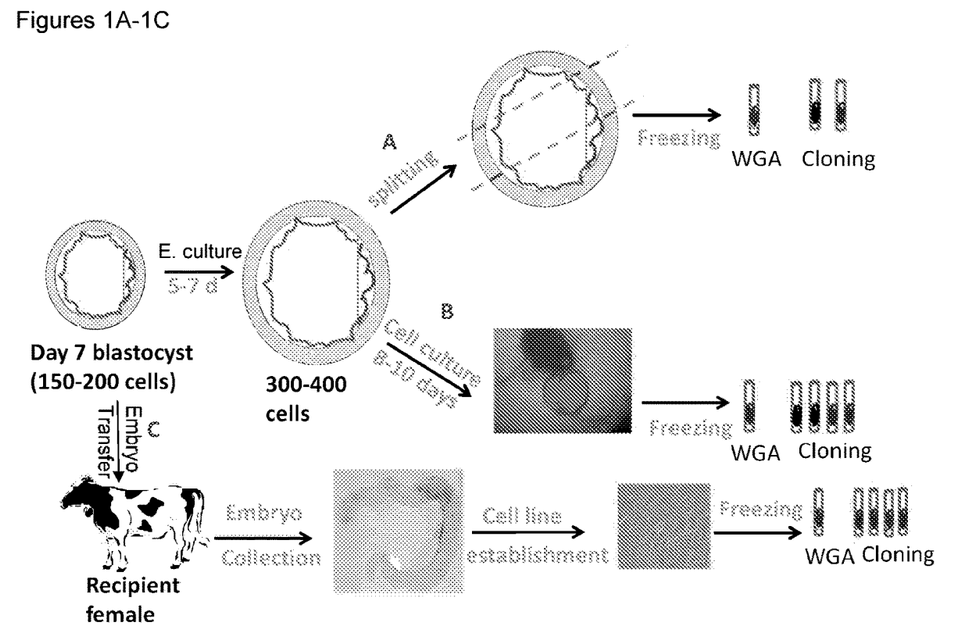
FIGS. 1A-1C illustrate methods of culturing whole embryos for expanding the cell numbers in the embryos.
Figure 2:
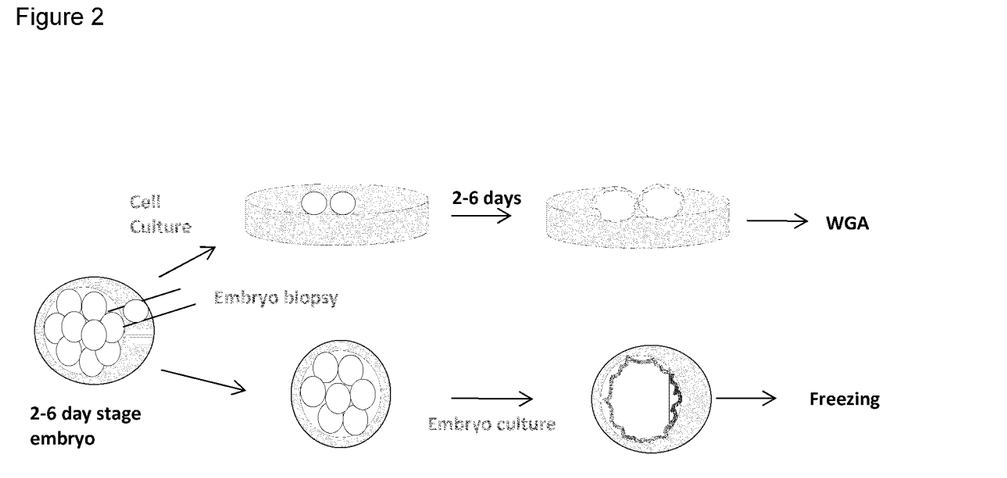
FIG. 2 illustrates the embryo biopsy and culture method.

Because freezing of developing embryos affects the calving efficiency, embryos are usually transferred fresh (i.e., without freezing) to recipient animals for production of offspring. Embryos are usually cultured in vitro for about 7 days after in vitro fertilization (IVF). When embryos are transferred to synchronized recipients at this stage, each embryo typically contains about 100-200 cells. The calving efficiency with this type of embryo transfer is approximately 40%, and the rate of obtaining superior animals from these offspring is very low. Improved methods for culturing embryos in vitro are disclosed herein to help solve this problem. More specifically, the time for culturing embryos in vitro may be extended by one week, two weeks, three weeks, one month, or longer to expand the cell number in each embryo (FIG. 1).

Accordingly, in one aspect, the invention features a method for selecting a genetically desirable trait(s) in a mammal. The method may include the following steps: (a) culturing an embryo in vitro, wherein the embryo comprises from 1 to about 500 cells (e.g., from about 100 to about 200 cells, e.g., from about 150 to about 200 cells) at the onset of step (a); (b) dividing the embryos of step (a) into two or more aliquots; (c) subjecting at least one of the two or more aliquots of step (b) to a genetic analysis; and (d) selecting one or more aliquots from step (b) based on results obtained from step (c), wherein the selected one or more aliquots carry the genetically desirable trait(s).

In one embodiment, following step (a), the method may include transferring the embryo (i.e., the in vitro cultured embryo) into a recipient female. In some embodiments, the embryo is collected from the recipient female after about 10 to 40 days (e.g., after about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days post-transfer). In some embodiments, the embryo is collected from the recipient female after about 21-26 days post-transfer. In some embodiments, the embryo is collected from the recipient female after about 21 days post-transfer. In other embodiments, the embryo is collected from the recipient female after a time period of greater than 40 days post-transfer.

In another embodiment, the method further includes a step (e) of using one or more cells from the selected aliquots of step (d) to produce a genetically superior mammal. In some embodiments, step (e) includes a step of nuclear transfer. In some embodiments, the method further includes a step (f) of freezing the aliquots of step (c) above that are not subject to genetic analysis. In another aspect, the method may also include a step (g) of thawing the frozen aliquot(s)/embryo(s) of step (f).

In another embodiment, embryos may be cultured individually in vitro for two weeks or more after fertilization with a modified tissue culture medium (e.g., without any feeder cells) in one or more multi-well plates. At this stage, embryos may be attached to the surface of the tissue culture plate and each well may contain several thousand cells. In one embodiment, these cells may be divided into several portions by enzymatic treatment (e.g., trypsinization). The divided portions may be frozen in several vials and stored in liquid nitrogen.

In one embodiment, one portion of the cells may be subject to genetic tests before being frozen. In another embodiment, the portion of the cells may be frozen and thawed before being subject to genetic tests. The results of the genetic tests may be used to determine whether to further pursue the remaining portion of the frozen cells from the same embryo. In one embodiment, if the results from the genetic tests indicate that the embryo possesses certain genetic traits that are desirable, the remaining cells may be used to generate offspring using standard nuclear transfer technique that would likely demonstrate such phenotypes.

In one embodiment, the medium used for step (a) may contain trisodium citrate, myo-inositol and aminoacids (e.g., SOFaaci), supplemented with 15% fetal calf serum. In another embodiment, the medium used for step (a) is embryonic cell culture medium (EC1). In one embodiment, EC1 is used to culture the cells until the cells are attached to the plate. In another embodiment, EC1 may contain 50% of standard synthetic oviductal fluid (SOF, e.g., SOFaaci) medium and 50% of tissue culture medium containing D-minimum essential medium (D-MEM) supplemented with 0.1% (v/v) 2-mercaptoethanol, 1% (v/v) non-essential aminoacids, 1% (v/v) ITS (10 µg/ml insulin, 5.5 µg/ml transferrin and 6.7 ng/ml selenium), 5 ng/ml human leukemia inhibitory factor, 10 ng/ml; human basic fibroblast growth factor, 10 ng/ml human epidermal growth factor, 0.5% penicillin-streptomycin solution, and 20% fetal calf serum.

In another embodiment, embryonic cell culture medium for maintenance of culture (EC2) may be used after the cells have attached to the plate. In one embodiment, EC2 may contain D-MEM supplemented with 0.1% (v/v) 2-mercaptoethanol, 1% (v/v) non-essential aminoacids, 1% (v/v) ITS (10 µg/ml insulin, 5.5 µg/ml transferrin and 6.7 ng/ml selenium), 5 ng/ml human leukemia inhibitory factor, 10 ng/ml; human basic fibroblast growth factor, 10 ng/ml human epidermal growth factor, 0.5% penicillin-streptomycin solution, and 20% fetal calf serum.

In another embodiment, the freezing medium may be EC2 containing 20% dimethyl sulfoxide (DMSO) and from 40% to 80% FCS. For example, 200 µl of DMSO and 600 µl of FCS may be added to 1 ml of EC2 to form a freezing medium.

In another embodiment, the embryo of step (a) may contain about 100 to about 200 cells at the onset of step (a). In another embodiment, the embryo may contain about 300 to about 600 cells at the end of step (a). In another embodiment, the embryo may contain about 400 to about 800 cells at the end of step (a).

In another aspect, the invention features a method for selecting a genetically desirable trait in a mammal that includes the following steps: (a) removing one or more cells from each of a plurality of embryos; (b) culturing the one or more cells for about 2 to 6 days; and (c) subjecting the cultured cells of step (b) to a genetic analysis; (d) culturing the plurality of embryos of step (a) after said one or more cells have been removed; and (e) selecting one or more embryos from the plurality of embryos of step (d) based on results obtained from step (c), wherein the selected one or more embryos have a potential of developing into a mammal carrying the genetically desirable trait.

In one embodiment, step (a) is performed when the plurality of embryos is at the age of about 2 days to about 6 days post-fertilization.

In another embodiment, the method further includes a step (f) of freezing the embryos of step (d). In another embodiment, the method further includes a step (g) of thawing the frozen embryos of step (f).

In another embodiment, the embryo is cultured in a medium including about 15% FCS during step (a).

In an embodiment of any of the above aspects, embryos are cultured in vitro for at least about 5 days (e.g., for at least about 5, 6, 7, 8, 9, 10, 11, 12, 13, or 14 or more days) after IVF. In some embodiments, the embryos that have been cultured for at least about 5 days (e.g., for at least about 5, 6, 7, 8, 9, 10, 11, 12, 13, or 14 or more days) after IVF may be further cultured for at least about 5 days (e.g., about 5, 6, 7, 8, 9, 10, 11, 12 or more days). After this additional culturing period of at least about 5 days (e.g., about 5, 6, 7, 8, 9, 10, 11, 12 or more days), each embryo may contain approximately 300-400 cells. At this stage, the embryos may be divided into several aliquots (e.g., 2, 3, 4, 5, 6, 7, 8, 9, or 10 or more aliquots). In one embodiment, micromanipulation techniques may be used to divide the embryos (e.g., by splitting). In another embodiment, the aliquots may be frozen separately in freezing medium and stored, for example, in liquid nitrogen for further downstream analysis (e.g., additional genetic analysis) and/or usage (e.g., usage for cloning, e.g., using a nuclear transfer).

In an embodiment of any of the above aspects, at least one aliquot of the embryo may be subject to one or more genetic tests, including, but not limited to, whole genome analysis (WGA), gene expression profiling (e.g., gene expression profiling using microarray), sequencing of a coding region of a gene, sequencing of a non-coding region of a gene, and whole genome sequencing. The result of the genetic tests may be analyzed in order to determine whether to use the other aliquots from the same embryo. In one embodiment, if the result from the genetic tests indicates that the embryo possesses the desirable genetic traits, the other aliquots from the same embryo may be used to generate offspring. Under such a scenario, the resulting offspring will likely demonstrate the desirable traits. In another embodiment, if the result from the genetic tests indicates that the embryo most likely does not possess the desirable genetic traits, the remaining aliquots may not be further pursued.

Genetic tests may involve analyzing the DNA in the cells of the embryos. In one embodiment, microsatellite marker panels may be used to identify genetic traits that are highly polymorphic and amenable to standardization among laboratories performing these tests. See, e.g., Sherman et al. *Anim Genet.* 35(3): 220-6; Heyen et al. *Anim Genet.* 28(1): 21-27; U.S. Pat. No. 5,874,217; Ostrander et al. *Mammalian Genome.* 6: 192-195; Franscisco et al. *Mammalian Genome.* 7: 359-362). In another embodiment, single nucleotide polymorphisms (SNPs) may be utilized in the genetic test.

In an embodiment of any of the above aspects, the genetic analysis may include one or more of the assays listed below: whole genome analysis (WGA) to be used in genetic evaluation programs for farm animals, including but not limited to, beef cattle, dairy cattle, swine, and sheep; gene expression profiling using microarray; and sequencing of a coding region or a non-coding region of a gene, including whole genome sequencing of an individual animal.

In an embodiment of any of the above aspects, the trait may be coat color, hair color, hair length, eye color, marbling, tenderness, quality grade, muscle content, fat thickness, feed efficiency, red meat yield, average daily weight gain, disease resistance, disease susceptibility, feed intake, protein content, bone content, maintenance energy requirement, mature size, amino acid profile, fatty acid profile, milk production, milk quality, fertility, ovulation rate, conception rate, and susceptibility to infection by pathogens.

DETAILED DESCRIPTION OF THE INVENTION

The present disclosure provides methods for selecting embryos having desirable traits prior to nuclear transfer for cloning or implantation of embryos. Methods for extended culture of embryos are also disclosed. Extended culture of embryos enable the use of genetic tests for selecting embryos having desirable traits. Genetic tests, such as whole genome analysis (WGA), may be employed to identify an embryo that possesses desirable genetic characteristics.

WGA and other genetic tests that can be used for genomic selection are disclosed, for example, in Humblot et al. *Vet. Med. Int.* 2010, Article ID 192787; Ponsart et al. 28*th Annual Meeting AETE*. Saint Malo, France, Sep. 7-8, 2012; Schefers and Weigel. *Animal Frontiers.* 2(1): 4-9, 2012. The methods disclosed herein may be applied to many mammals, such as cattle, as well as in horses, dogs, cats, goats, sheep, bison, deer, donkeys, mules, swine, hogs, among others.

In one embodiment, a female animal may be induced to superovulate, eggs may be collected from the superovulated female. The collected eggs may be fertilized in vitro using sperms from a suitable male animal. The fertilized eggs may be cultured in vitro to allow the cells numbers to expand in the embryos.

In one embodiment, embryos may be cultured while the genetic tests are being performed on a portion of the cells from the same embryos. If the test results are positive, the cultured embryos may be transferred to a recipient for production of offspring. Alternatively, cells from these positive embryos may be used for cloning to produce genetically superior animals. In another embodiment, methods are disclosed for expanding and freezing of embryonic cells. Genetic tests may be performed on a portion of the expanded cells. If the test results are positive, the remaining cells from the same embryos may be thawed and used to produce offspring.

In another embodiment, biopsy sample(s) may be obtained from embryos that have been cultured for about 3-7 days after fertilization. General methods of embryo biopsy are known in the art and disclosed, for example, in Polisseni et al. *Fertility and Sterility.* 93(3): 783-788, 2010; Lopes et al. *Theriogenology.* 56(9): 1383-1392, 2001. The biopsied cells may be cultured individually to expand the cells for about 2-10 days, or even longer. The expanded cells from the biopsy sample may be subject to genetic test, such as whole genome analysis (WGA), while the rest of the embryos are cultured. Multiple displacement amplification (MDA) is one type of WGA technique, which may be used to increase the amount of DNA from biopsies for analysis (see, e.g., Lauri et al. *Genomics.* 101(1): 24-29, 2013). After WGA is performed, superior embryos may be selected to produce calves based on the WGA results from corresponding biopsy samples. The embryos may be continuously cultured after the biopsy is performed, for example, until WGA is completed on the biopsied sample. Such embryos may be cultured for about 1 week (or, in some instances, longer, e.g., 2 or 3 weeks) post-biopsy before they are frozen. The fate of the frozen embryos may be decided depending upon results from the WGA of the biopsied sample. If the genetic tests indicate that the corresponding embryos may develop into an animal possessing superior traits, the frozen embryos may be used for cloning or implantation to generate offspring that possess such traits.

In another embodiment, the whole embryo may be cultured in vitro for 5-7 extra days after the approximately 7-day post-fertilization culturing period. At this stage, each embryo typically contains approximately 300-400 cells. These embryos may be divided into several aliquots using micromanipulation techniques and frozen separately in freezing medium and stored in liquid nitrogen for further downstream analysis and usage (see FIG. 1A).

In another embodiment, the embryos may be cultured individually for about 2-6 weeks in vitro with modified tissue culture medium in multi-well plates containing mitotically arrested mono-layer of feeder cells (see FIG. 1B). At this stage, embryos are attached to the surface of the tissue culture plate and each well contains several thousand cells. These cells may be divided into several portions by enzymatic treatment and frozen in several vials and stored in liquid nitrogen.

Thus, the several vials of frozen cells may be derived from the same well and are clonally expanded from the same embryo. One of these vials may be used for genetic tests, such as whole genome analysis (FIG. 1).

In another embodiment, embryos that have been in culture for 5-9 days (e.g., 7 days) may be transferred into synchronized recipient females using standard non-surgical embryo transfer methods (see FIG. 1C). These embryos may be collected about 10-40 days (e.g., about 21-26 days, e.g., about 21 days) after this transfer to establish cell lines. Each of these cell lines may be divided into several portions by enzymatic treatment, frozen in several vials, and stored in liquid nitrogen for future use.

Based on the results of this analysis, genetically superior frozen vials may be selected and used as nuclear donor cells to clone calves using established nuclear transfer procedures. These methods of culturing the embryos and producing calves by nuclear transfer may significantly reduce the production of genetically less valuable animals by increasing (e.g., by at least 5%, 10%, 15%, 20%, 25%, 30%, 40%, 50%, 60%, 70%, 80%, 90%, or 100% or more) the selection intensity and accuracy of selection and decreasing (e.g., by at least 5%, 10%, 15%, 20%, 25%, 30%, 40%, 50%, 60%, 70%, 80%, 90%, or 100% or more) the generation interval.

For purpose of this disclosure, genetic test(s) may include analyzing data associated with one or more genetic characteristics in individual embryos or cells obtained from individual embryos. In one embodiment, the methods and systems of the present disclosure may utilize genetic information obtained from individual embryos to identify embryos that may possess desirable traits. The genetic information may include but is not limited to single nucleotide polymorphisms (SNPs), insertions, deletions, inversions and other mutations.

As used herein, the term "polymorphism" refers to an allelic variant that occurs in a population, which may be a single nucleotide difference present at a locus, or an insertion or deletion of one, a few or many consecutive nucleotides, or an inversion. A single nucleotide polymorphism (SNP) may be characterized by the predominance of certain nucleotides at a specific locus of a genome in a certain population. Under most circumstances, less than all four nucleotides (i.e., adenosine, cytosine, guanosine or thymidine) predominate at a particular locus. For instance, a specific locus in a genome of a given population may contain either a cytosine or thymidine at the polymorphic site and thus two of the four nucleotides predominate at this particular locus. However, polymorphism of one, two, three or four nucleotides may exist. It will be recognized that, while the methods disclosed herein are exemplified by the detection of SNPs, the disclosed methods or others known in the art similarly can be used to identify other types of polymorphisms, such as an insertion or a deletion, which typically involve more than one nucleotide.

A "single nucleotide polymorphism" or "SNP" typically occurs at a polymorphic site occupied by a single nucleotide, which is the site of variation between allelic sequences. The site is usually flanked by highly conserved sequences of the allele. For instance, the highly conserved sequences may vary in fewer than $1/100$ or $1/1000$ members of the population. A single nucleotide polymorphism usually arises due to a substitution of one nucleotide for another at the polymorphic site. Single nucleotide polymorphisms may also result from a deletion of a nucleotide or an insertion of a nucleotide relative to a reference allele.

According to one aspect of the present disclosure, a genetic test may include detecting at least one SNP in one or more genes implicated in certain genetic traits. For instance, the method may include determining the identity of a nucleotide at one or more specific positions of one or more genes, and comparing the identity to the nucleotide identity at corresponding positions of a reference allele.

The term "haplotype" refers to the genetic constitution of an individual chromosome. Haplotype may refer to only one locus or to an entire genome. The term "haplotype" may also refer to a set of SNPs that are statistically related.

For purpose of this disclosure, the term genotyping may be used to refer to the process of determining the genetic information an individual animal carries at one or more positions in the genome. For example, genotyping may include determination of which allele or alleles an individual carries for a single SNP or the determination of which allele or alleles an individual carries for a plurality of SNPs.

Genetic tests may be performed to determine one or more genetic characteristics or traits. For instance, a plurality of assay compositions may be used to identify a plurality of nucleotide markers, such as SNPs. In one embodiment, the presence or absence of a nucleotide polymorphism may be detected by polymerase chain reaction (PCR) followed by nucleotide sequencing. The presence or absence of a plurality of nucleotide polymorphisms may be detected by performing PCR assays using a panel of primers followed by nucleotide sequencing. In another embodiment, a polymorphism may be identified, at least in part, by using the polymerase chain reaction without sequencing.

PCR reactions may be performed simultaneously using assay plates or a flat-block thermal cycler. PCR primers may be pre-labeled using fluorescent dye such that the fluorescence output may be read using a computer-based imaging system. Using such a design, high-throughput cost-efficient analysis of hundreds or thousands of polymorphic sites may be assayed simultaneously.

A sample for practicing the method of the present disclosure may be obtained from a cell, a portion or a biopsy of an embryo or from the culture medium in which the embryos are cultured. Optionally, call rates of the PCR amplified DNA samples may be determined to evaluate the genotyping quality (e.g., genotyping accuracy) in WGA using standard techniques known in the art (see, e.g., Lewis and Knight. *Cold Spring Harbor Protoc.* 297-306, 2012). In one embodiment, the sample is a nucleic acid sample. The nucleic acid sample may be deoxyribonucleic (DNA) acid or ribonucleic acids (RNA). The DNA may be genomic DNA, or reversely transcribed cDNA. The DNA may be coding or non-coding sequences of a gene or whole genome sequence of an individual mammal. Methods of genetic engineering, which may include but are not limited to PCR, DNA hybridization, DNA sequencing, vector construction, recombinant DNA techniques, may be found in the literature, such as Maniatis et al. *Molecular Cloning A Laboratory Manual.* Cold Spring Harbor Laboratory, N.Y. (1989), which is incorporated herein in its entirety by reference. By way of example, assays for WGA may include but are not limited to, the use of the Illumina Bovine SNP50 and Bovine LD assays (Illumina, Inc., San Diego, Calif.) for generation of genomic enhanced genetic evaluations.

It is to be noted that the term "a" or "an" refers to one or more of an entity; for example. "an animal," is understood to represent one or more animals. As such, the terms "a" (or "an"), "one or more," and "at least one" may be used interchangeably in this disclosure.

The term "about" means substantially the same with a deviation of no more than 10-20%.

EXAMPLES

The following examples are provided for purposes of illustration of embodiments only and are not intended to be limiting. The reagents, chemicals and other materials are presented as exemplary components or reagents, and various modifications may be made in view of the foregoing discussion within the scope of this disclosure. Unless otherwise specified in this disclosure, components, reagents, protocol, and other methods used in the system and the assays, as described in the Examples, are for the purpose of illustration only. It is to be understood that although per-pubertal heifers are used in the Examples, the disclosed methodology may be applied to mature heifers as well.

Example 1

Whole Embryo Culture in Vitro and Splitting of Embryos

Oocytes were collected from pre-pubertal heifers. Following a 7-day culturing window that is standard practice in the field, embryos were cultured in vitro for an additional 5-7 days in standard embryo culture medium (e.g., synthetic oviductal fluid (SOF), e.g., SOF with amino acids, sodium citrate, and myo-inositol (SOFaaci)) with 15% Fetal calf serum. At this stage, each embryo contained approximately 300-400 cells (FIG. 1). These embryos were divided into three aliquots using micromanipulation techniques (FIG. 1A). The three aliquots were frozen separately in freezing medium (EC2 with 20% DMSO and 60% FCS) and stored in liquid nitrogen for further downstream analysis and usage.

Using the method described above, several aliquots of cells from the same embryo are generated. One or more of these aliquots are used for whole genome analysis (WGA) or other types of genetic analysis (FIG. 1A). Based on the results of the genetic tests, frozen cells corresponding to the cells that possess the desirable traits are selected and used as nuclear donor cells to clone calves using well-established nuclear transfer procedures. This method of culturing the embryos and producing calves by nuclear transfer may reduce the production of less valuable animals by increasing the selection intensity and accuracy of selection and decreasing the generation interval.

Example 2

Extended Culture of Whole Embryo in Vitro

Jersey females were super-ovulated, and oocytes aspirated and matured in vitro per standard protocols. After maturation, oocytes were inseminated in vitro using semen from different Jersey bulls. After fertilization, presumptive zygotes were cultured for 7-8 days. Expanded blastocyst stage embryos were then selected and cultured individually in multi-well plates containing modified tissue culture medium without any feeder cells for approximately 10 days (see FIG. 1B). Once the cultured embryos were attached to the surface of the tissue culture plate and started to divide, the culture media was replaced once every 4 days until cell colony monolayers were established. Table 1 below shows the number of cell lines established with cultured whole Jersey embryos using this method.

TABLE 1

Cell line establishment with Jersey embryos

| Date of oocyte aspiration | Sire/donor combination | No. of embryos cultured | No. of cell lines established in 8-10 days |
|---|---|---|---|
| Mar. 22, 2012 | Camilo/6528 | 6 | 4 |
| | Camilo/6810 | 9 | 9 |
| Apr. 5, 2012 | Zuma/6528 | 6 | 3 |
| | Zuma/6810 | 2 | 1 |
| Apr. 12, 2012 | Camilo/7242 | 1 | 1 |
| | Camilo/7005 | 2 | 0 |
| | Camilo/7124 | 14 | 4 |
| Total | | 40 | 22 |

After approximately 10 days in culture, the established cell colony monolayers were mechanically disrupted into cell clumps by repeated pipetting. These clumps of cells were pelleted and the pellet was dissolved in freezing medium containing 20% DMSO and 40% serum. This suspension with clumps was divided into 3-5 vials and frozen using slow freezing. These frozen vials were stored in liquid nitrogen.

Using the method described above, several vials of cells that were clonally expanded from one embryo were generated. One or more of these vials were used for WGA. Based on the results of this analysis, genetically superior frozen vials are selected and used as nuclear donor cells to clone calves using well-established nuclear transfer procedures.

Example 3

Embryo Transfer to Recipient Mothers

Jersey females were super-ovulated, and oocytes aspirated and matured in vitro per established protocols. After maturation, oocytes were inseminated in vitro using semen from different Jersey bull. After fertilization, presumptive zygotes were cultured for seven days. On day 7, embryos were selected, graded, and transferred to a recipient mother, with each recipient mother receiving 3-5 embryos (1-3 embryos per uterine horn).

Embryos were collected between pregnancy days 21-26. Briefly, recipient mothers were confined in a cattle chute and given an epidural block of 2% procaine. A sterile 24-gauge Foley catheter was inserted through the cervix into the uterine body and ViGro complete flush solution (Bioniche Animal Health Inc., Pullman, Wash.) supplemented with 16 µl/ml of antibiotic-antimycotic (Gibco, Grand Island, N.Y.) and 8 µl ml fungizone (Gibco, Grand Island, N.Y.) was flushed through the uterus non-surgically. Upon recovery, embryos were isolated from the uterine flush medium under a stereomicroscope.

Jersey cell lines were established as follows. Briefly, flushed embryos were transported to the laboratory in Dulbecco's phosphate buffered solution (DPBS) with 16 µl/ml of antibiotic-antimycotic (Gibco, Grand Island, N.Y.), 5 µl/ml penicillin Streptomycin (Sigma, St. Louis, Mo.) and 8 µl/ml fungizone (Gibco). Embryos were rinsed in DPBS and finely chopped into pieces with a scalpel blade. The fibroblasts were separated from the tissue pieces by standard trypsinization procedure using TrypLE (Gibco). The cells were seeded onto 25-cm vented tissue culture flasks (BD) in DMEM (Gibco) supplemented with 10% FCS (fetal calf serum, Hyclone, Logan, Utah), 0.003% β-mercaptoethanol (Gibco) and penicillin/streptomycin solution (Sigma). On day four of seeding, the cells were harvested, using TrypLE solution and reseeded onto 75 cm² tissue culture flasks. After 3-4 days of culture, cells were harvested and approximately one hundred thousand cells were used for DNA isolation. The remaining cells were frozen in DMEM with 10% FCS and DMSO (Sigma).

Table 2 below summarizes the number of Jersey embryo cell lines established by this embryo transfer method.

TABLE 2

Summary of Embryo transfers, collections and cell line establishments

| Date of transfer | No. of embryos | No. of recipients | No. of embryos collected | No. of cell lines established | No. of usable cell lines frozen |
|---|---|---|---|---|---|
| 24 Jan. 2013 | 19 | 5 | 10 | 10 | *8 |
| 31 Jan. 2013 | 9 | 3 | 7 | 7 | 7 |
| 14 Feb. 2013 | 12 | 3 | 3 | 3 | 3 |
| 20 Feb. 2013 | 16 | 4 | 10 | 10 | 10 |
| 7 Mar. 2013 | 18 | 5 | 8 | 8 | 8 |
| 13 Mar. 2013 | 3 | 1 | 2 | 2 | 2 |
| 21 Mar. 2013 | 6 | 2 | 2 | 2 | 2 |
| 27 Mar. 2013 | 3 | 1 | 5 | 5 | 5 |
| 10 Apr. 2013 | 12 | 3 | 6 | 6 | 6 |
| 24 Apr. 2013 | 17 | 4 | 8 | 8 | 8 |
| 8 May 2013 | 9 | 2 | 6 | 6 | 6 |
| 10 May 2013 | 11 | 3 | 3 | 3 | 3 |
| 24 May 2013 | 17 | 4 | 3 | 3 | 3 |
| 7 Jun. 2013 | 3 | 1 | 0 | 0 | 0 |
| Total | 155 | 41 | 73 | 73 | 71 |

*Fungal contamination was observed in two cell lines after establishment and they were discarded.

The DNA samples isolated from cell lines were submitted for whole genome analysis (WGA) and genotyping through Geneseek, Inc. (Lincoln, Nebr.) to the animal improvement program laboratory at USDA. The results are summarized in Table 3 below.

TABLE 3

DNA sample analysis and selection of cell lines

| Date of sample submission | No. of DNA samples | No. of samples analyzed successfully (%) | No. of cell lines with JPI > 210 (%) |
|---|---|---|---|
| 4 Apr. 2013 | 28 | 23 (82.14) | 1 (4.3) |
| 29 Apr. 2013 | 17 | 17 (100) | 1 (5.9) |
| 29 May 2013 | 13 | 13 (100) | 0 |
| 24 Jun. 2013 | 13 | 13 (100) | 3 (23.1) |
| Total | 71 | 66 (92.95) | 5 (7.6) |

After genotyping these cell lines, five cell lines were selected based on the general Jersey Performance Index (JPI) in Table 4. Each of these cell lines (FL065, FL062, FL064, FL017, and FL036) were determined to have a favorable JPI score of 210 or greater.

TABLE 4

Summary of the top five selected cell lines

| Cell line ID | JPI Gen | CM Gen | NM Gen | PTAT Gen | MILK Gen | FAT Gen | PRO Gen | PL Gen | SCS Gen | DPR Gen | UDC Gen | Haplotypes |
|---|---|---|---|---|---|---|---|---|---|---|---|---|
| FL065 | 251 | 750 | 680 | 2.1 | 880 | 75 | 41 | 6.5 | 2.86 | 1.2 | 6.13 | JH1T JH1__PC.N JHPT JHP__PC.N |
| FL062 | 224 | 688 | 623 | 1.8 | 669 | 65 | 34 | 6.2 | 2.86 | 1.6 | 5.02 | JH1T JH1__PC.N JHPT JHP__PC.N |
| FL064 | 221 | 708 | 618 | 1.0 | 501 | 63 | 33 | 6 | 2.73 | 1.5 | 4.92 | JH1T JH1__PC.N JHPT JHP__PC.N |
| FL017 | 215 | 692 | 607 | 0.9 | 470 | 60 | 31 | 5.8 | 2.72 | 1.9 | 4.35 | JH1T JH1__PC.N JHPT JHP__PC.N |
| FL036 | 210 | 594 | 571 | 1.4 | 909 | 32 | 29 | 6.6 | 2.76 | 1.1 | 5.76 | JH1T JH1__PC.N JHPT JHP__PC.N |

Two cell lines were used for making cloned embryos using the standard nuclear transfer procedure as described earlier. The in vitro embryo development of these cell lines looked similar to that of other fibroblast cell lines (Table 5).

TABLE 5

Clone embryo development in vitro with some of the established cell lines

| Cell line ID | Total reconstructed | No. of fused couplets (%) | No. of blastocysts developed on day 7 (%) |
|---|---|---|---|
| FL010 | 224 | 150 (66.9) | 26 (17.3) |
| FL010 | 103 | 68 (66.0) | 14 (20.6) |
| FL065 | 165 | 115 (69.7) | 11 (9.6) |
| FL065 | 156 | 92 (58.9) | 38 (41.3) |
| Total | 648 | 425 (65.6) | 89 (20.9) |

A total of 16 embryos from cell line FL065 were transferred to synchronized recipient females on 4 and 18 Sep. 2013 (Table 5). The pregnancy status of these recipients will be confirmed approximately at 40 and 60 days of gestation using ultrasonography and thereafter by rectal palpation every other month.

TABLE 6

Embryo transfers and pregnancies with cell line FL065

| Cell line ID | No of recipients implanted | Pregnant at (%) 40 days | Pregnant at (%) 60 days |
|---|---|---|---|
| FL065 | 11 | 6 (55) | ND |
| FL065 | 5* | ND | ND |
| Total | 16 | | |

*These animals will be pregnancy checked on 22 Oct 2013.
ND: Not detected and in progress.

Example 4

Embryo Biopsy and Culture

Biopsy sample(s) from Day 2-7 embryos were obtained and the biopsied cells (e.g., 4-6 cells from each embryo) were cultured individually. The remaining embryos were also cultured separately from the biopsied cells. Standard SOFaaci medium was used. The biopsied cells were allowed to expand for 1-6 days. Since few cells result in limited amounts of genomic DNA, only a limited number of markers can be tested. To evaluate this, call rates of the amplified DNA samples using Bovine SNP50 bead chip with cells collected after biopsy and cells cultured for a day or two after biopsy were determined (Table 7). DNA amplified from whole embryos and fetal fibroblast cell lines were used as control.

TABLE 7

Call rates of the samples analyzed

| Sample ID | DNA amplified from | Call rates (%) |
|---|---|---|
| F21 | Fibroblast cells | 99.0 |
| E11 | Whole embryo | 94.6 |
| B1 | Biopsy 6-8 cells | 79.8 |
| B2 | Biopsy 6-8 cells | 81.9 |
| B3 | Biopsy 6-8 cells | 36.7 |
| B4 | Biopsy after two days of culture | 75.5 |
| B5 | Biopsy after two days of culture | 80.0 |

When the call rates of the biopsy samples are optimized (e.g., are uniformly above 80%) for accurate genetic analysis, we may use the expanded cells from the biopsy for WGA, while freezing the biopsied embryos. Based on the results from WGA, superior embryos are selected to produce calves.

Other Embodiments

Although each of the embodiments described above has been illustrated with various components having particular respective orientations, it should be understood that the system and methods as described in the present disclosure may take on a variety of specific configurations with the various components being located in a variety of positions and mutual orientations and still remain within the spirit and scope of the present disclosure. Furthermore, suitable equivalents may be used in place of or in addition to the various components, the function and use of such substitute or additional components being held to be familiar to those skilled in the art and are therefore regarded as falling within the scope of the present disclosure. Therefore, the present examples are to be considered as illustrative and not restrictive, and the present disclosure is not to be limited to the details given herein but may be modified within the scope of the appended claims.

All patents, patent applications, patent application publications, and other publications cited or referred to in this specification are herein incorporated by reference to the same extent as if each independent patent, patent application, patent application publication or publication was specifically and individually indicated to be incorporated by reference. Such patent applications specifically include U.S. Provisional Patent Application No. 61/716,294, filed Oct. 19, 2012, from which this application claims benefit.

What is claimed is:

1. A method for producing a non-human mammalian progeny having a genetically desirable trait, the method comprising:
    (a) culturing a non-human mammalian embryo in vitro to establish a candidate cell line comprising from about 300 to about 800 cells;
    (b) dividing the cells of the candidate cell line into two or more aliquots;
    (c) subjecting a first aliquot from the two or more aliquots to a genetic analysis to test for the presence of one or more genes and/or one or more polymorphisms associated with the genetically desirable trait, wherein the presence in the first aliquot identifies the candidate cell line as having the genetically desirable trait;
    (d) if the first aliquot does not comprise the genetically desirable trait, repeating steps (a)-(c) with a subsequent non-human mammalian embryo until the candidate cell line having the genetically desirable trait is identified; and
    (e) producing, using cells from a second aliquot from the two or more aliquots from the candidate cell line identified as having the genetically desirable trait, the non-human mammalian progeny having the genetically desirable trait.

2. The method of claim 1, wherein the candidate cell line comprises from about 400 to about 800 cells at the end of step (a).

3. The method of claim 2, wherein the embryo comprises from about 100 to about 200 cells at the onset of the culturing step.

4. The method of claim 1, wherein the production of the progeny involves transferring a nucleus of a cell from the second aliquot into an enucleated oocyte.

5. The method of claim 1, comprising freezing the cells of at least one aliquot from the two or more aliquots that has not been subjected to the genetic analysis.

6. The method of claim 5, wherein the cells that are frozen are later thawed.

7. The method of claim 1, wherein the genetic analysis comprises one or more assays selected from the group consisting of: whole genome analysis (WGA); gene expression profiling using microarray; sequencing of a coding region of the one or more genes; sequencing of a non-coding region of the one or more genes; and whole genome sequencing.

8. The method of claim 1, wherein the two or more aliquots consist of between two and ten aliquots.

9. The method of claim 1, wherein the one or more polymorphisms are each individually selected from the group consisting of: single nucleotide polymorphisms, insertions, deletions, inversions, and mutations.

10. The method of claim 1, wherein the one or more polymorphisms include single nucleotide polymorphisms.

11. A method for producing a bovine progeny having a genetically desirable trait, the method comprising:
    (a) culturing a bovine embryo in vitro for 5 to 9 days;
    (b) following the culturing of the embryo, transferring the cultured embryo into a recipient female;
    (c) collecting the post-transfer embryo from the recipient female;
    (d) culturing the cells from the post-transfer embryo in vitro to establish a candidate cell line;
    (e) dividing the cells of the candidate cell line into two or more aliquots;
    (f) subjecting a first aliquot from the two or more aliquots in step (e) to a genetic analysis to test for the presence of one or more genes and/or one or more polymorphisms associated with the genetically desirable trait, wherein the presence in the first aliquot identifies the candidate cell line as having the genetically desirable trait;
    (g) if the first aliquot does not comprise the genetically desirable trait, repeating steps (a)-(f) with a subsequent bovine embryo until the candidate cell line having the genetically desirable trait is identified; and
    (i) producing, using cells from a second aliquot from the two or more aliquots from the candidate cell line identified as having the genetically desirable trait, the bovine progeny having the genetically desirable trait.

12. The method of claim 11, wherein the collecting of the fetus occurs about 10 to 40 days post-transfer.

13. The method of claim 11, wherein the collecting of the fetus occurs about 10 to 30 days post-transfer.

14. The method of claim 11, wherein the collecting of the fetus occurs at about 14 to about 19 days post-transfer.

* * * * *

UNITED STATES PATENT AND TRADEMARK OFFICE
CERTIFICATE OF CORRECTION

| | | |
|---|---|---|
| PATENT NO. | : 10,927,411 B2 | Page 1 of 1 |
| APPLICATION NO. | : 14/436664 | |
| DATED | : February 23, 2021 | |
| INVENTOR(S) | : Poothappillai K. Kasinathan et al. | |

It is certified that error appears in the above-identified patent and that said Letters Patent is hereby corrected as shown below:

In the Claims

Column 14, Line 35:
"(i)"
Should read:
--(h)--

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*